(12) United States Patent
Kim

(10) Patent No.: US 7,252,012 B2
(45) Date of Patent: *Aug. 7, 2007

(54) DEVICE AND METHOD FOR TESTING PAVING MATERIALS

(75) Inventor: Sang-Soo Kim, Athens, OH (US)

(73) Assignee: Ohio University, Athens, OH (US)

( * ) Notice: Subject to any disclaimer, the term of this patent is extended or adjusted under 35 U.S.C. 154(b) by 39 days.

This patent is subject to a terminal disclaimer.

(21) Appl. No.: 10/524,907

(22) PCT Filed: Aug. 22, 2003

(86) PCT No.: PCT/US03/26459

§ 371 (c)(1),
(2), (4) Date: Feb. 17, 2005

(87) PCT Pub. No.: WO2004/019177

PCT Pub. Date: Mar. 4, 2004

(65) Prior Publication Data

US 2006/0117863 A1   Jun. 8, 2006

Related U.S. Application Data

(60) Provisional application No. 60/405,532, filed on Aug. 23, 2002.

(51) Int. Cl.
*G01N 3/00* (2006.01)
(52) U.S. Cl. ...................................................... 73/803
(58) Field of Classification Search ................ 73/803

See application file for complete search history.

(56) References Cited

U.S. PATENT DOCUMENTS 4,127,840 A * 11/1978 House ............................ 338/4

(Continued)

FOREIGN PATENT DOCUMENTS

JP          05087716         4/1993

(Continued)

OTHER PUBLICATIONS

Bahia, et al. Characterization of Modified Asphalt Binders in Superpave Mix Design, NCHRP Report 459, Transportation Research Board, National Research Council, Washington, DC (2001).

(Continued)

*Primary Examiner*—Max Noori
(74) *Attorney, Agent, or Firm*—Calfee, Halter & Griswold LLP

(57) ABSTRACT

A device and method for directly measuring the critical temperatures for thermal cracking of asphalt binders. The exemplary comprises a metal ring, a strain gauge attached to the inner surface of the ring, an environmental chamber, one or more signal amplifiers, and a data acquisition system such as a laptop computer running suitable data analysis software. A thermocouple may also be attached to the inside of the tube to closely monitor the ring temperature. A mold that is also a component of the present invention is used to create a circular asphalt binder test specimen. When properly cast the specimen encircles the metal ring. The specimen and ring are placed within the environmental chamber for analysis. Development of thermal stress (induced by temperature reduction within the environmental chamber) within the asphalt binder test specimen is monitored by the strain gauge and the cracking temperature is directly determinable from the strain reading.

15 Claims, 4 Drawing Sheets

U.S. PATENT DOCUMENTS

| | | | |
|---|---|---|---|
| 4,425,808 | A | 1/1984 | Rand |
| 4,498,231 | A | 2/1985 | Rand |
| 4,507,975 | A * | 4/1985 | Bittner et al. ............ 73/861.12 |
| 4,763,531 | A * | 8/1988 | Dietrich et al. ........ 73/862.044 |
| 4,821,584 | A * | 4/1989 | Lembke ................... 73/862.68 |
| 5,036,709 | A | 8/1991 | McRae |
| 5,248,200 | A | 9/1993 | Walsh |
| 5,394,753 | A | 3/1995 | Moriyoshi |
| 5,659,140 | A | 8/1997 | Jakob et al. |
| 5,712,431 | A | 1/1998 | Vilendrer |
| 5,844,053 | A * | 12/1998 | Nishida ..................... 525/476 |
| 5,904,760 | A | 5/1999 | Hayner |
| 5,905,212 | A * | 5/1999 | Moses et al. .......... 73/862.451 |
| 6,408,683 | B2 | 6/2002 | Bahia et al. |
| 6,792,815 | B2 * | 9/2004 | McDearmon et al. .. 73/862.041 |
| 2004/0019177 | A1 | 1/2004 | Brugel et al. |
| 2005/0178209 | A1 * | 8/2005 | Kim ............................ 73/803 |

FOREIGN PATENT DOCUMENTS

| | | |
|---|---|---|
| JP | 06174614 | 6/1994 |

OTHER PUBLICATIONS

Bouldin, et al. Predicting Thermal Cracking of Pavements From Binder Properties: Theoretical Basis and Field Validation, Journal of Association of Asphalt Paving Technologists, (2000), vol. 69, pp. 455-496.

Hibbeler, R.C. Mechanics of Materials, Third Edition, Prentice-Hall, Upper Saddle River, New Jersey (1997), pp. 136-138, 143-144, 152.

Hills, J.F. Predicting the Fracture of Asphalt Mixes by Thermal Stresses, Institute of Petroleum, (1974), vol. 74-014.

Hossain, et al. Quantifying Early-Age Stress Development and Cracking in Low Water-to-Cement Concrete Using the Restrained-Ring Test with Acoustic Emission, Presented at 82d Transportation Research Board Meeting (TRB 2003 Annual Meeting CD/ROM).

Kennedy, et al. Superior Performing Asphalt Pavements (Superpave): The Product of the SHRP Asphalt Research Program, SHRP-A-410, (1994), Strategic Highway Research Program, National Research Council, Washington, DC.

Masad, et al. Modeling and Experimental Measurements of Strain Distribution in Asphalt Mixes, Journal of Transportation Engineering, (2001), vol. 127, No. 6, pp. 477-485.

Roy, et al. Low-Temperature Binder Specification Development, Transportation Research Record, (2001), 1766, pp. 7-14.

Van Der Poel, C. A General System Describing the Visco-Elastic Properties of Bitumens and its Relation to Routine Test Data, Journal of Applied Chemistry, (1954), vol. 4, pp. 221-236.

Notification of Transmittal of the International Search Report or the Declaration, dated Mar. 3, 2004 for PCT/US03/26459.

Shah et al., "A Method to Predict Shrinkage Cracking of Concrete", *ACI Materials Journal*, Jul.-Aug. 1998, pp. 339-346.

* cited by examiner

DEVICE AND METHOD FOR TESTING PAVING MATERIALS

CROSS-REFERENCE TO RELATED APPLICATIONS

This patent application claims the benefit of U.S. Provisional Patent Application Ser. No. 60/405,532 filed on Aug. 23, 2002 and entitled "device and Method for Testing Paving Materials," the disclosure of which is incorporated as if fully rewritten herein.

TECHNICAL FIELD OF THE INVENTION

The present invention relates generally to devices for testing the characteristics of construction materials such as asphalt and concrete and specifically to a circular metal device and associated method for characterizing the failure modes of asphalt binders.

BACKGROUND OF THE INVENTION

Asphalt is a general term that refers to the various bituminous substances that are used extensively for paving and road-making. Asphalt binders function as adhesion promoters for asphalt mixtures or aggregates and are typically comprised of naturally occurring hydrocarbons or petroleum distillate residue with or without polymer or chemical modifiers. In the paving industry, the term "aggregate" is used for a mass of crushed or uncrushed stone, gravel, sand, etc., predominantly composed of individual particles, but in some cases including clays and silts. The performance characteristics of asphalt binders are of particular importance in roadway construction. Understanding the limitations of the materials used for roadway construction permits the design and construction of roadways that are more stable, durable, and that offer greater safety to the user of the roadway.

Low temperature thermal shrinkage cracking is one of four major failure modes in asphalt pavement, together with rutting, fatigue cracking, and moisture damage. Thermal shrinkage cracking in asphalt pavement occurs when the thermal tensile stress within the asphalt pavement that results from temperature drop exceeds the strength at that temperature. Thermal cracks typically appear as transverse cracks (pavement cracks perpendicular to the direction of traffic) at regular intervals in the field pavements.

Historically, low temperature thermal cracks have been controlled by limiting the asphalt binder stiffness. Assuming similar asphalt binder tensile strengths and coefficients of thermal expansion/contraction, the binders with a higher stiffness will crack at a higher temperature than softer binders. Because an accurate and easy to use measuring instrument was not available, the cracking temperature or the limiting low temperature stiffness of asphalt binder had been extrapolated from consistencies measured at higher temperatures, such as penetrations at 5 and 25° C., viscosity at 25° C., or ring-and-ball softening point (50-60° C.). Hill, J. F., Inst. Petroleum, vol. 74-014 (1974) and Van der Poel, C., Journal of Applied Chemistry, vol. 4, 221-236 (1954).

In the United States, the Association of American State Highway and Transportation Officials (AASHTO) has published and implemented a series of performance graded ("PG") binder specifications. These specifications were the result of the Strategic Highway Research Program (SHRP) which was conducted from 1987-1994. The SHRP/AASHTO system for specifying asphalt binders is unique in that it is a performance-based series of specifications. Various binders are categorized on the basis of the climate and attendant pavement temperatures at which the binder is expected to operate.

Under this system, physical property requirements remain the same, but the temperature at which the binder must attain the properties changes. For example, a binder graded as PG 64-22 possesses adequate physical properties up to 64° C., which would be the high pavement temperature corresponding to the climate in which the binder is expected to operate. Similarly, the PG 64-22 binder possesses adequate physical properties down to at least minus 22° C. Thus, as illustrated by this example, the thermal characteristics of an asphalt binder are central to this grading system.

As will be appreciated by those skilled in the art, low-end temperatures of PG grading are typically determined by utilizing one or more of several known systems including the Bending Beam Rheometer (BBR) and/or the Direct Tension Tester (DTT). While effective at generating useful data, these systems are complex, require the performance of numerous calculations, require the testing of many specimens, do not directly measure the temperature at which the specimen fails, and are often very time consuming and expensive to perform. Thus, there is a need for a low-cost device and method that quickly and accurately characterizes the critical thermal characteristics of asphalt binder and aggregate specimens.

SUMMARY OF THE INVENTION

These and other deficiencies of the prior art are overcome by the present invention, the exemplary embodiment of which provides a device and method for directly measuring the critical temperatures for thermal cracking of asphalt binders. In the broadest sense, the exemplary embodiment of the present invention comprises a metal ring, a strain gauge attached to the inner surface of the ring, an environmental chamber, one or more signal amplifiers, and a data acquisition system such as a laptop computer running suitable data acquisition and analysis software. A thermocouple may also be attached to the inside of the tube to closely monitor the ring temperature.

A mold that is also a component of the present invention is used to create a circular asphalt binder test specimen. When properly cast the specimen encircles the metal ring. The specimen and ring are placed within the environmental chamber for analysis. Development of thermal stress (induced by temperature reduction within the environmental chamber) within the asphalt binder test specimen is monitored by the strain gauge and the cracking temperature is directly determinable from the strain reading.

Further advantages of the present invention will become apparent to those of ordinary skill in the art upon reading and understanding the following detailed description of the preferred embodiments.

BRIEF DESCRIPTION OF THE DRAWINGS

The accompanying drawings, which are incorporated into and form a part of the specification, schematically illustrate one or more exemplary embodiments of the invention and, together with the general description given above and detailed description of the preferred embodiments given below, serve to explain the principles of the invention.

DETAILED DESCRIPTION OF THE INVENTION

Figure 1:
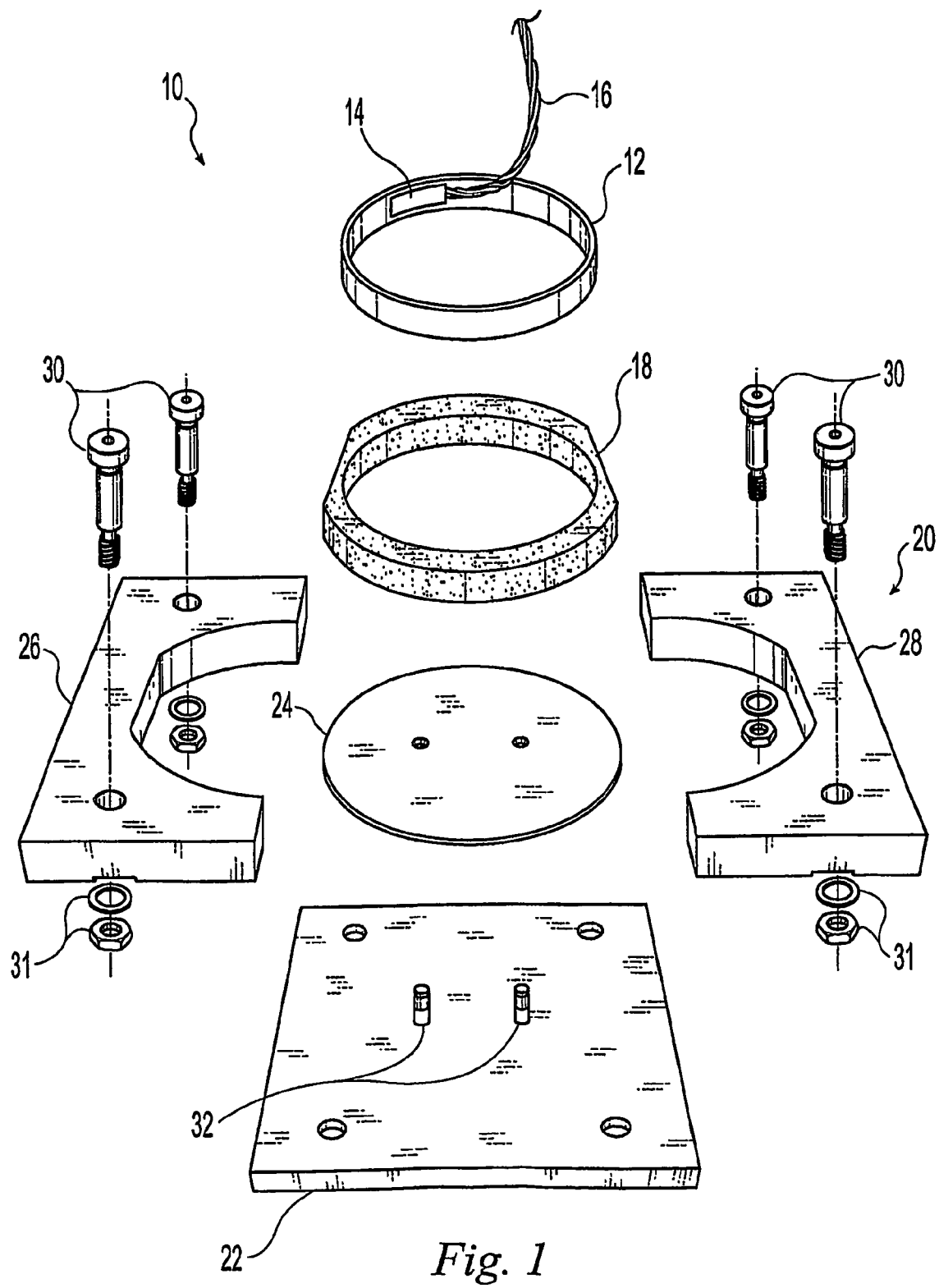
FIG. 1 is an exploded, perspective view of the mold and ring portion of the system of the present invention.

Reference Numerals
10 materials testing device
12 ring
14 strain gauge
15 thermocouple
16 lead wires
18 test specimen
20 mold
22 base plate
24 centering plate
26 first specimen support
28 second specimen support
30 shoulder bolts
31 washer/nut combination
32 dowel pins
40 signal amplifier
50 processor
60 environmental chamber
70 materials testing system I. Overview The present invention provides a device and method for inducing a thermal crack in a test specimen in a manner that simulates the conditions experienced by asphalt binder found in the field. This device can be used to measure the cracking temperature and the thermal stress experienced by the test specimen under experimental conditions. The present invention directly measures the critical temperatures for thermal cracking of asphalt binders by using the dissimilar coefficients of thermal expansion for asphalt binders and common metals, such as aluminum. Aluminum has a modulus of elasticity that is about one third of steel and consequently shows three times larger strain response, i.e., better resolution, for the same stress development.

In the most generic sense, the exemplary embodiment of the present invention comprises a metal ring, a strain gauge attached to the inner surface of the ring, an environmental chamber, one or more signal amplifiers, and data acquisition system. A thermocouple may also be attached to the inside of the tube to closely monitor the ring temperature. An asphalt binder test specimen is molded onto the outside of the aluminum ring prior to analysis of the specimen. Development of thermal stress, due to temperature reduction, within an asphalt binder test specimen is monitored by the strain gauge and the cracking temperature is directly determinable from the strain reading. It should be noted that thermal cracking of asphalt pavement is significantly influenced not only by binder properties but also by mix properties such as binder contents, gradation, mastic composition, etc. Furthermore, strain distribution within asphalt binders under compressive and thermal loading is not uniform. Despite these variables, the method of the present invention assumes uniform stress-strain conditions for typical hot mix asphalt and is intended to grade asphalt binders according to their performance to minimize premature thermal cracking.

Asphalt binders have much larger coefficients of thermal expansion/contraction ($170$-$200 \times 10^{-6}$/° C.) than aluminum ($24 \times 10^{-6}$/° C.). As the environmental temperature drops, the differential thermal contraction (i.e., more rapid contraction of asphalt binder than that of aluminum) creates thermal stress and eventually thermal cracks appear in the specimen. Strain in the aluminum tube caused by this thermal stress is measured by the electrical strain gauge and used to calculate stress in the asphalt binder. When the test specimen cracks, the accumulated thermal stress is relieved and is shown as a sudden drop in the strain reading. The cracking temperature of the asphalt binder is directly determined as the temperature where the sudden drop of measured strain occurs. By varying the geometry of asphalt binder specimens, the field strain and strain rate conditions can be closely simulated by the experimental method of this invention. The effects of aggregate properties on the critical temperature can be also closely simulated by adjusting the wall thickness of the aluminum ring.

The present invention is suitable for characterizing materials such as neat or modified asphalt binders and other similar viscoelastic materials including certain polymers. Using the device and methods of this invention, asphalt and other thermoplastic polymers can be heated, formed into a ring-shaped specimen, and tested for certain desired characteristics.

II. System Components

Figure 2:
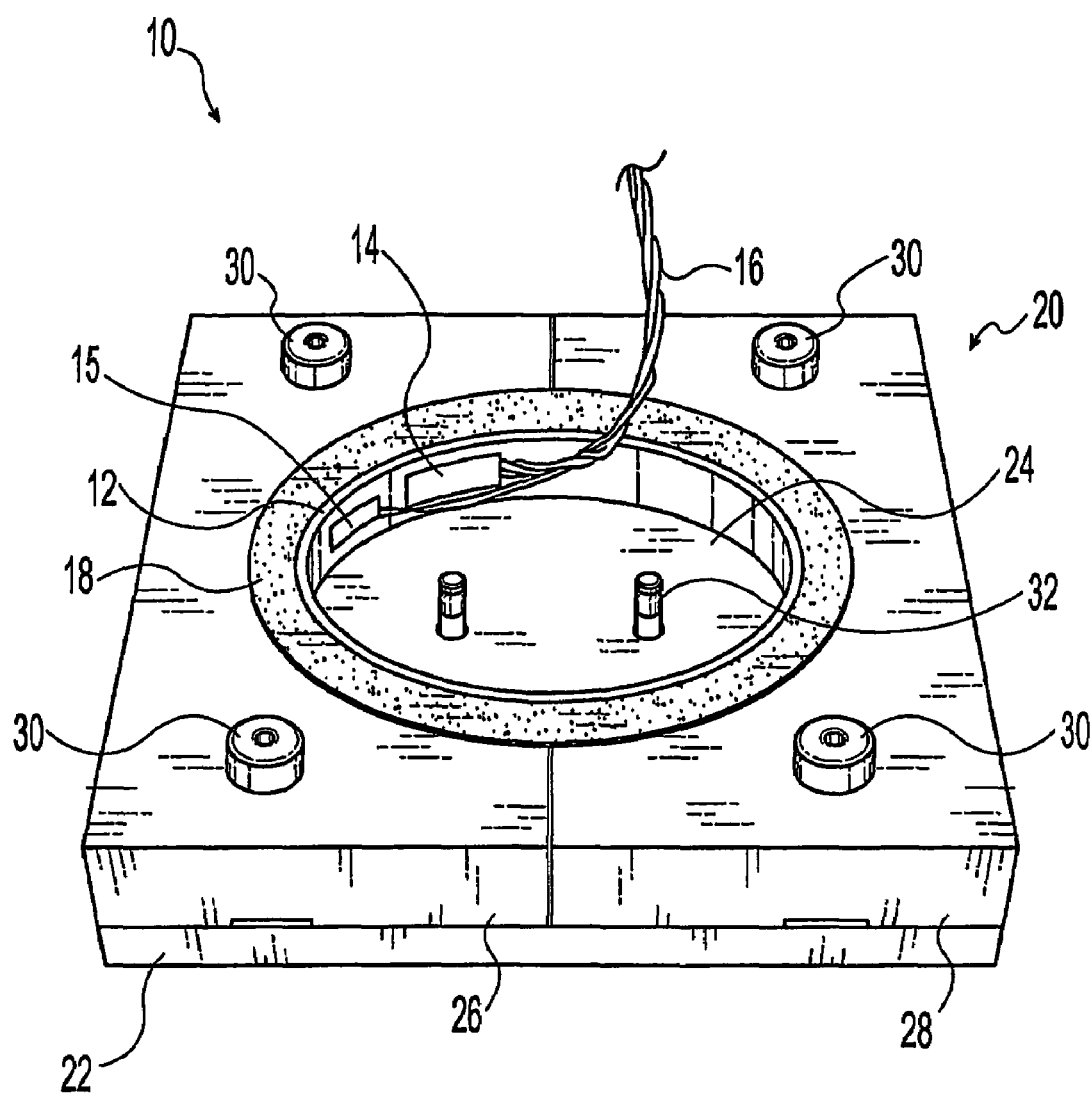
FIG. 2 is a perspective view of the mold and ring portion of the system of the present invention.
Figure 3:
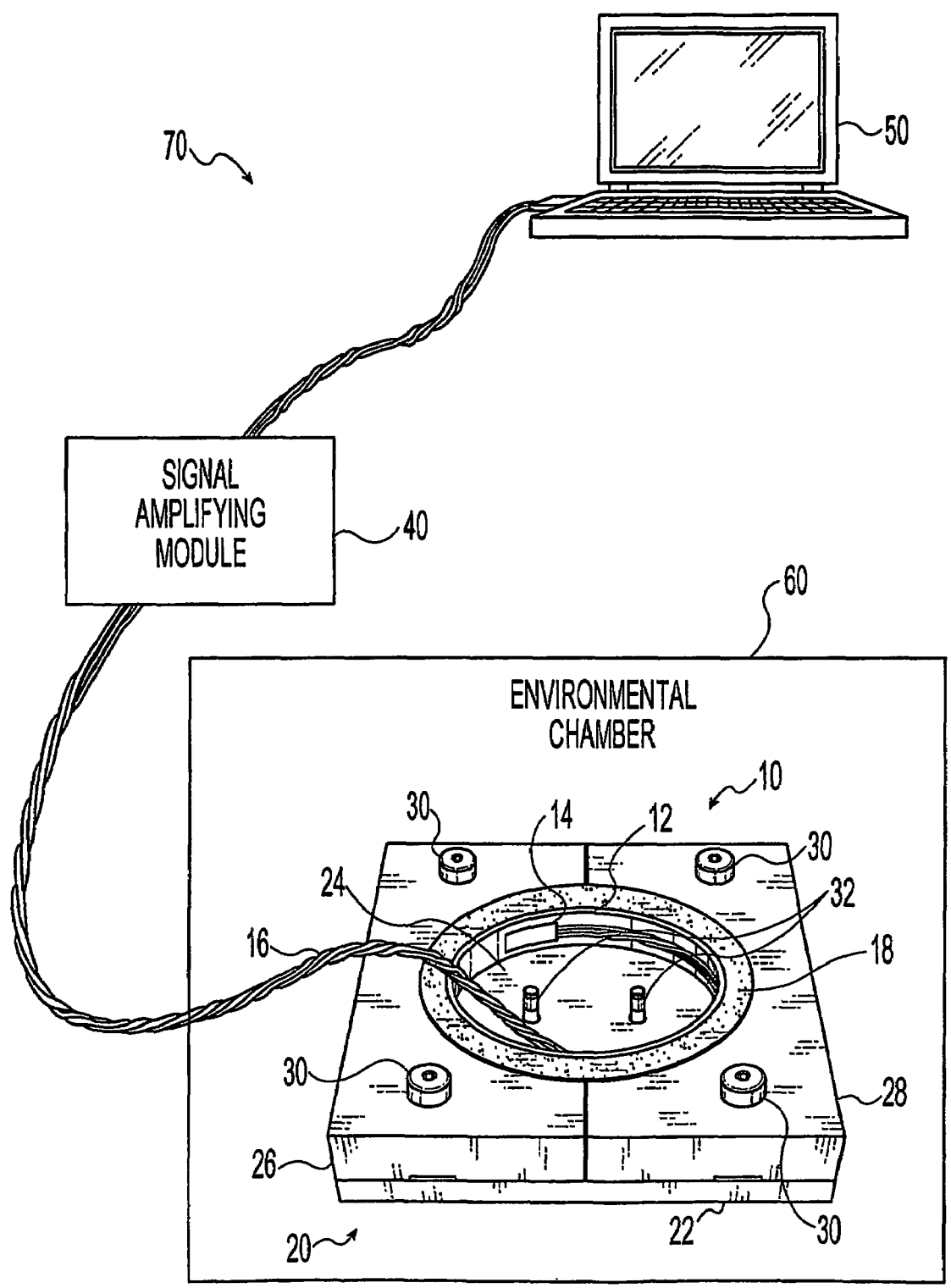
FIG. 3 is a perspective view of the system of the present invention illustrating the system components of an exemplary embodiment.

As shown in FIG. 1-2, materials testing device 10 includes a ring 12, a strain gauge 14, and lead wires 16. Materials testing device 10 also comprises a mold 20 for creating the test specimen 18. As best shown in FIG. 3, system 70 also includes a signal amplifier 40 for amplifying the electrical signal generated by the strain gauge, a data acquisition system or processor 50 for gathering data and performing the desired calculations, and an environmental chamber 60 for controlling the temperature to which the test sample is subjected. Each of the system components is described in greater detail below.

A. Ring

In an exemplary embodiment of the present invention, ring 12 is constructed from aluminum tubing having an outer diameter of about 50.8 mm, a height of about 12.7 mm, and a thickness of about 1.65 mm. Test rings having a variety of wall thickness can be utilized with the present invention to effectively simulate and characterize the thermal cracking phenomenon experienced by pavement materials in the field. Alternate embodiments of ring 12 utilize aluminum rings having wall thicknesses of approximately 0.005, 0.035, and 0.049 inches (0.013, 0.089, and 0.125 cm). Although aluminum is used in the exemplary embodiment, other types of metal, metal alloys, or other materials that have strain characteristics that can be accurately measured, i.e., about 100 microstrains, are compatible with the present invention. The suitability of various metals for use with the present invention can be determined empirically by placing an asphalt specimen outside of a metal test ring (0.5 inch×0.25 inch cross-section area) and measuring the strain experienced by the ring when the specimen reaches the limits of its tensile strength at a low temperature.

B. Strain Gauge

Mechanical strain experienced by ring 12 while specimen 36 contracts is detected by one or more electrical strain gauges 14 that are attached to the interior surface of ring 12. Data gathered from the strain gauge is transmitted through lead wires 16 to processor 50. In general, strain gauges can be described as mechanical transducers which are used to measure body deformation, or strain, applied to the area of a rigid body. Electrical resistance strain gauges are strain sensitive when bonded to the surface of a test material. When the strain gauge is stretched or compressed, its electrical resistance changes in direct proportion to the strain. By measuring the change in electrical resistance experienced by the strain gauge, the strain experienced by a test material in may be quantified.

In an exemplary embodiment, a precision strain gauge available from the Micro-Measurements Division of Vishay Measurements Group (CEA-13-500UW-120) is used to obtained experimental data useful for characterizing a test specimen. This type of gauge is a general purpose Constantan strain gauge commonly used in experimental stress analysis. Each commercially purchased gauge of this type is supplied with a fully encapsulated grid and exposed copper-coated integral solder tabs and has the following properties: (i) a temperature range of −75° C. to 205° C.; (ii) a gauge length of 0.500 inch; (iii) self-temperature compensated; (iv) strain limit: approximately 5% of the gauge length; (v) fatigue life: $10^5$ cycles at ±1800 μm/m; and (vi) a resistance of 120 Ohms. In alternate embodiments, a smaller size strain gauge (⅛ inch gauge length, EA-13-125BZ-350 also available from Micro-Measurements) with specifications similar to the gauge described above is utilized. Smaller size strain gauges facilitate the placement of centering plate 24 during preparation of the test specimen. The mechanical strain experienced by ring may also be detected with other forms of measuring devices, such as Linear Variable Differential Transduces (LVDTs) placed inside of the ring 12.

C. Thermocouple

As shown in FIG. 2, one or more thermocouples 15 may be attached to the inner surface area of ring 12 or near the test specimen. These thermocouples detect and measure temperature changes experienced by the ring and the specimen 18. In an exemplary embodiment, a Type T thermocouple (SA-T-72-SC) from Omega Engineering Inc. having the following properties is used: (i) response time: less than 0.3 seconds; (ii) temperature range: minus 60° C. to 175° C.; (iii) high temperature polymer lamination and fiberglass reinforced polymer layers; (iv) length: 72 inches; (v) alloy combination: positive (+) lead: copper and negative (−) lead: Constantan copper-nickel; (vi) and an error of (above 0° C.): greater of 1.0° C. or 0.75%.

D. Mold

As shown in the Figures, a mold 20 is a basic component of the present invention. Mold 20 may be manufactured from a variety of metals including aluminum and steel. Mold 20 is used to create substantially circular test specimens for use with materials testing device 10. In an exemplary embodiment, mold 20 further includes base plate 22, centering plate 24, and first and second specimen supports 26 and 28. Centering plate 24 is mounted on the top surface of base plate 22 and held in the proper position by dowel pins 32. The specimen supports are also mounted on the top surface of base plate 22 and are secured to the base plate by shoulder bolts 30. Shoulder bolts 30 are secured to the base plate by washer/nut combination 31. In an exemplary embodiment, base plate 22 is about 10.2 cm in length and about 10.2 cm in width. Centering plate 24 is about 47.50 mm in diameter and about 3.18 mm thick. The two specimen supports are about 12.7 mm thick.

Ring 12 is placed around centering plate 20 prior to casting the test specimen in the mold. An exemplary embodiment of the assembled mold creates a ring-shaped test specimen which is about 2.5 inches (6.35 cm) in diameter. The walls of the ring-shaped test specimen are about 0.25 inches thick. In an alternate embodiment of the present invention, the inner walls of specimen supports 26 and 28 are not a smooth arc-shape, but include a straight-edge portion (see FIG. 1). The length of straight-edge portion may be varied by the user of this invention based on the type and composition of the asphalt pavement being tested. Presumably, tests specimens molded to have straight edges more accurately replicated the thermal contraction experienced by materials in use in the field.

E. Signal Amplifiers

In the exemplary embodiment of the present invention, strain detected by the strain gauge(s) and temperature changes detected by the thermocouple(s) are amplified by signal amplifiers, typically referred to as "modules", prior to being routed to the data processing unit. Modules suitable for the testing and characterization described herein include the AD-1 808FB-1 Analog Input Module and a handheld digital thermometer (similar to HH81A thermometer from Omega Engineering Inc.).

The AD-1 808FB-1 Analog Input Module, manufactured by Optim Electronics Corporation of Germantown, Md., interacts with the strain gauges. Each 808FB-1 has eight independent channels for measuring one-quarter, one-half, and full bridge strain gauges. This module operates as two groups of four channels. The groups are divided into channels 0-3 and 4-7, with each channel receiving the same gain, excitation and voltage. Each parameter is jumper selectable. Jumper settings provides for addressing 2, 5, or 10-volt excitation voltage sources, calibration voltage, gain and filter frequency for each bank of channels along with other parameters. Each analog input module requires a Screw Terminal Block (STB). STBs provides for an easy connection between the sensors and the analog input cards. The STB 808FB-1 has two major functions. First, it allows for an interface between the lead wire of the one-quarter, one-half and full bridge strain gauges. Second, it provides for bridge completion of the one-quarter and one-half bridge strain gauges. Interfacing is provided for eight channels. Five screw terminals are allocated for each channel. Each channel requires that jumpers be set for one-quarter, one-half or full bridge application. In the present invention, a handheld digital thermometer (similar to HH81A thermometer from Omega Engineering Inc.) was used to read the signal (temperature) manually from the thermocouple placed with the test specimen.

In an alternate embodiment, a compact data acquisition system from the National instruments (NI) is utilized to collect strain and temperature data during the test. The alternate data acquisition system consists of the NI Lab-VIEW, NI PCI-6036E multifunction I/O, NI SCC-TC02 thermocouple input modules, and NI SCC-SG01 strain gauge input modules. LabVIEW is a graphical development environment with built-in functionality for data acquisition, instrument control, measurement analysis, and data presentation and provides the flexibility of a programming language without the complexity of traditional development environments.

The NI PCI-6036E has sixteen 16-bit analog inputs and two 16-bit analog outputs. In addition, it has 8 digital I/O lines and two 24-bit, 20 MHz counter/timers. Depending on the hard drive, the PCI-6036E can stream-to-disk at rates up to 200 kS/s.

The NI SCC-SG01 consists of four models of 2-channel strain gauge input modules, each designed for a particular strain gauge configuration: 120 ohm quarter-bridge, 350 ohm quarter-bridge, half-bridge, and full-bridge. Each channel of these modules includes an instrumentation amplifier, a 1.6 kHz lowpass filter, and a potentiometer for bridge offset nulling. Each SCC-SG01 module also includes a single 2.5 V excitation source.

The NI SCC-TC02 is a single-channel module for conditioning a variety of thermocouple types, including J, K, T, B, E, N, R, and S, and millivolt inputs with a range of ±100 mV. The SCC-TC modules include a 2 Hz lowpass noise filter, instrumentation amplifier with a gain of 100, and buffered outputs. The input circuitry of the SCC-TC modules also includes high-impedance bias resistors for open-thermocouple detection as well as handling both floating and ground-referenced thermocouples. The SCC-TC modules include an onboard thermistor for cold-junction compensation.

F. Processor/Data Acquisition System

In the exemplary embodiment of the present invention, a Megadac 5414AC data acquisition system, manufactured by Optim Electronics Corporation of Germantown, Md., was used to monitor and record strain sensor response presented in the exemplary test data. The Megadac 5414AC is a 16-bit system with 256 megabytes of acquisition and storage memory. Data, i.e., time and strain gauge signals in microstrain, was collected at one sample per second per sensor and filtered at 100 Hz. A portable computer with windows operating system was used to operate the Megadac. The self-contained Megadac data acquisition system was controlled through an interactive IEEEE-488 communications bus. Optim provided its own Test Control Software (TCS) for the data acquisition system. TCS is windows based software used to communicate, setup, and acquire data from the Megadac. Using TCS, real time display of test time and the strains were presented in tabular and graphic forms during the test. Megadac is also capable of storing sensor identification and data confirmation information as well as provide an output format for the final results. Settings for the strain gauges used in this invention were 5 volts excitation and 2.115 gauge factor.

Data collected by Megadac were exported as text format and read into Micrsoft Excel spread sheet. Time and temperature data collected manually were combined with the Megadac data in Excel for determination of the cracking temperature and the tensile strength of the specimen by plotting temperature versus strain.

An alternate embodiment of this system utilizes the National Instruments, LabVIEW and NI PCI-6036E multifunction I/O to collect test time, strains, and temperature data simultaneously. NI LabVIEW is a graphical development environment with built-in functionality for data acquisition, instrument control, measurement analysis, and data presentation performing similar to the Megadac system. LabVIEW provides the flexibility of a programming language without the complexity of traditional development environments. The NI PCI-6036E has sixteen 16-bit analog inputs and two 16-bit analog outputs. In addition, it has 8 digital I/O lines and two 24-bit, 20 MHz counter/timers. Depending on hard drive, the PCI-6036E can stream-to-disk at rates up to 200 kS/s.

G. Environmental Chamber

During the analysis of a test specimen, materials testing device 10 is placed in an environmental chamber 60 that simulates the low temperature extremes experienced by asphalt binders and other materials in the field. Environmental chambers suitable for use with the present invention include any programmable refrigeration device that permits the user to lower the internal temperature of the chamber at a constant rate to below minus 50° C. using air or liquid fluid as cooling medium. Suitable liquid mediums in a bath for temperature control include ethanol, methanol, and glycol-methanol mixtures.

III. Specimen Preparation and Analysis

A. Experimental Method

In accordance with the teachings of the present invention, asphalt binder specimens may be prepared and analyzed by the following exemplary method.

1. Assemble one or more aluminum (or steel) molds. Uniform 6.35 mm thick circular asphalt binder specimens are desirable for this exemplary method. Preferably, samples are prepared in triplicate.
2. Apply (lightly) high vacuum grease to the exterior surface of ring 12 to prevent bonding between ring 12 and specimen 18 and to reduce any friction between the asphalt binder and the ring surface during the de-molding process (i.e., removal of the specimen from the mold).
3. Place thin plastic film (e.g., transparency film for a laser printer) on top of base plate 22 to facilitate removal of specimen 18 following casting; position centering plate 20 and tighten dowel pin(s) 32; and attach specimen supports 26 and 28 with the shoulder bolts 30.
4. On the inside, arced surface of specimen supports 26 and 28, place a strip of plastic. Light application of vacuum grease to both ends of plastic strip facilitates the placement of the plastic strip on specimen supports.
5. Heat a quantity of asphalt binder to about 150° C. until the binder becomes sufficiently fluid-like. Pour the liquefied binder into the ring-shaped area in the mold between the specimen supports and the ring. Because the liquefied binder contracts as it cools, it may be necessary to slightly overfill the mold to create a specimen having the desired size characteristics.
6. Allow the specimen to cool to room temperature. Using a heated spatula trim off any excess asphalt binder from the mold. Place the de-molded specimens (in triplicate) in the microprocessor controlled environmental chamber and pre-treat for 30 minutes at minus 10° C.
7. Connect the electrical strain gauge and the thermocouple first to the input module (i.e., signal amplifier) and then to processor 50.
8. Lower the temperature from minus 10 to minus 40° C. at a rate of 10° C. per hour.
9. Run a data acquisition program, assign proper gauge factor for each electric strain gauge, and set the desired data collection time interval. The gauge factor of 2.115 for the strain gauges used was input into the Megadac system in the exemplary method.
10. Measure and record (i) the temperature of the chamber and the specimens (using a thermocouple placed in a blank or dummy specimen) and (ii) the strain readings of the test specimens at a rate of one reading per second. Note: When a relatively slow cooling rate (e.g., 10° C./hour) is used, a single thermocouple is adequate for gathering data; however, if a more rapid cooling rate is used, extra thermocouples imbedded in extra asphalt specimens may be needed because at the more rapid cooling rate, the temperature inside of the asphalt binder will be significantly different from the temperature of the environmental chamber.

11. Determine the cracking temperature and calculate the thermal stress experienced by the test specimens.

Temperature calibration is done once before testing specimens. As the temperature drops, length of metal foil in the strain gauge and the aluminum ring change, resulting in varying strain readings of an empty ring at different temperatures. Temperature calibration is done by collecting test time, strain of the empty ring (without asphalt binder), and temperature as temperature is lowered as in the actual specimen testing. The difference of the strains of ring 12 with and without binder specimen is the strain attributed to the thermal load due to the differential contraction between the asphalt binder and the aluminum ring.

Data (time and strains) collected by Megadac were exported as text format and read into a Micrsoft Excel spread sheet. Time and temperature were collected manually and combined with the Megadac data in Excel for determination of the cracking temperature and the tensile strength of the specimen by plotting temperature versus strain. The data in Excel spread sheet program were in tabular form with time in second, temperature in centigrade Celsius (° C.), and strain in microstrain (με).

B. Cracking Temperature

Figure 4:
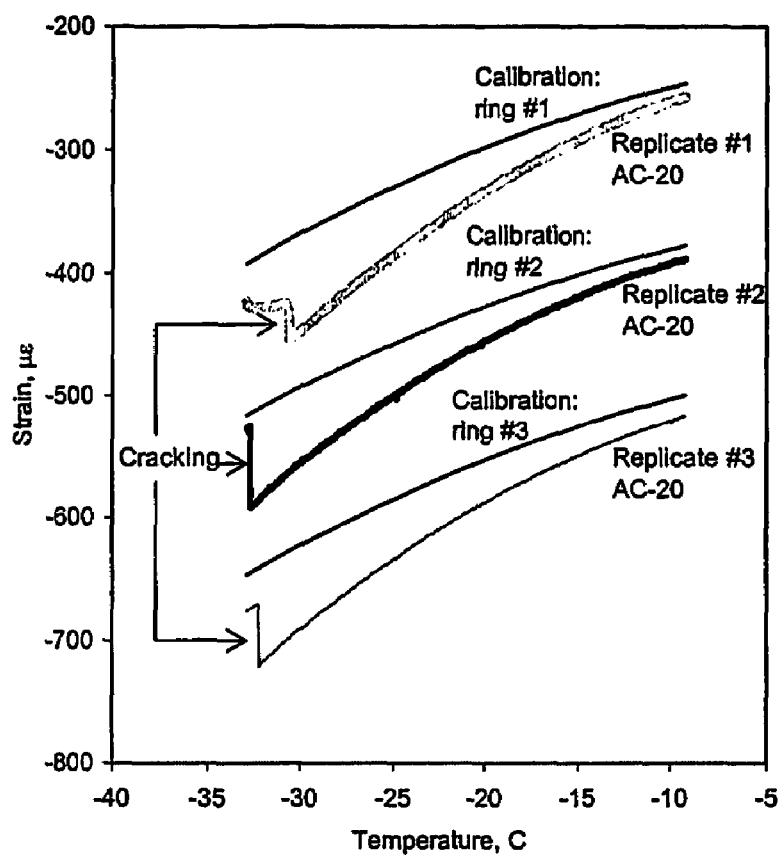
FIG. 4 is a data plot showing the uncorrected strain of the specimen (sample reading) and the baseline reading (temperature calibration with empty aluminum ring) versus temperature.

For determination of the cracking temperature, no calculation is necessary. A plot of uncorrected strain (or corrected for temperature by subtracting baseline strain determined from the ring temperature calibration) versus temperature is constructed. As the temperature drops, the contraction of the asphalt binder is considerably greater than that of the aluminum ring, and thus the ring experiences compressive strain. Because the stiffness (modulus) of the binder specimen rapidly increases as the temperature is lowered, stresses on the binder specimen and the ring also increases as the temperature is lowered. When the stress on the asphalt binder specimen reaches the tensile strength of the binder, the specimen cracks (fails) and the stress is relieved. This release of stress in the specimen is shown as the abrupt reduction of strain experienced by the ring. The cracking temperature directly correlates to this abrupt relief of the compressive strain. FIG. 4 is a graphic representation of this effect. In this experiment, strain readings of test specimens were taken every one second and were plotted together with the temperature calibration of three rings in FIG. 4. The cracking temperature of the specimens ranges from −30.6 to −32.7° C.

C. Thermal Stress

Figure 5:
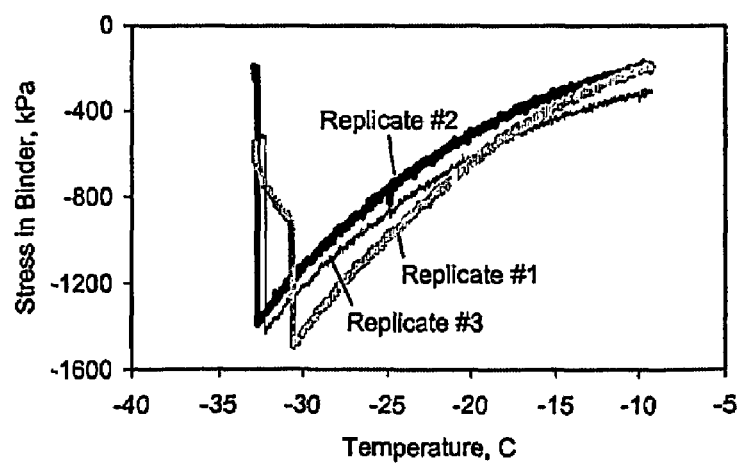
FIG. 5 is a data plot showing thermal stress development versus temperature during an experimental analysis of an asphalt binder specimen.

For the calculation of thermal stress, a temperature correction is required. As with all other materials, strain gauges also contract and expand as the temperature changes, thereby affecting the strain readings at different temperatures. A baseline temperature scan is performed for each ring 12, i.e., testing empty aluminum ring. Then, the corrected strain, the force in the aluminum ring, and the thermal stress in the binder specimen can be determined as:

$$\epsilon_{corr} = \epsilon_{test} - \epsilon_{calib}$$

$$F_{ABCD} = \epsilon_{corr} \cdot E_{ABCD} \cdot A_{ABCD}$$

$$\sigma_b = F_{ABCD}/A_b$$

where, $\epsilon_{corr}$=strain gauge reading corrected for temperature $\epsilon_{test}$=strain gauge reading of the aluminum ring tested with the asphalt binder εcalib=strain gauge reading of the aluminum ring tested without an asphalt binder $F_{ABCD}$=thermal force in the aluminum ring $E_{ABCD}$=modulus of elasticity of the aluminum ring $A_{ABCD}$=cross-sectional area of the aluminum ring $A_b$=cross-sectional area of the asphalt binder $\sigma_b$=thermal stress in the asphalt binder FIG. 5 shows thermal stress developing in the three test specimens during the experiment. The tensile strength of the specimen at the cracking temperature ranges from 1390 kPa to 1500 kPla. Note: Young's modulus (modulus of elasticity) of aluminum ($10.0 \times 10^3$ ksi,), was used for the calculating the thermal stress in this example.

IV. Summary

The present invention utilizes the dissimilar coefficients of thermal expansion and contraction of asphalt binders and various metals. Asphalt binders have much larger coefficients of thermal expansion and contraction than aluminum. When asphalt binders are subjected to falling temperatures, the differential thermal contraction (i.e., the more rapid contraction of asphalt binder than that of aluminum) creates thermal stress and eventually thermal cracks in the asphalt binder. When an asphalt specimen is placed around ring 12, the contraction of the specimen caused by a decrease in external temperature creates strain in the aluminum of the ring. This strain is measured by the electrical strain gauge 14, and may be used to calculate the stress experienced by the asphalt binder specimen.

When the asphalt specimen reaches the limit of its tensile strength, the specimen will crack, and the release of the thermal stress in the specimen can be detected as a sudden decrease in the measurable strain experienced by ring 12. Thus, the cracking or failing temperature of the asphalt binder is directly determinable as the temperature at which the sudden drop of measured strain occurs. The device of the present invention can induce a thermal crack within a binder specimen in a manner similar to what occurs to pavement in the field. The device can be used to measure the cracking temperature and the thermal stress.

Compared with the existing methods to determine the critical temperature for thermal cracking of an asphalt binder, the present invention offers the following advantages: (i) easy determination of the thermal cracking potential of asphalt binders without elaborate assumptions and calculations; (ii) the test method of this invention may accommodate various field environmental conditions and mixture properties by adjusting the cooling rate and specimen/test geometry; (iii) determination of thermal stress and strength with simple calculations; (iv) fast measurement: because a single temperature scan is required in testing multiple specimens for the cracking temperature determination, the exemplary method takes less time than others methods which require multiple single-specimen tests at different temperatures; (v) simultaneous testing of many specimens: theoretically, up to 60-90 specimens can be placed and tested together in the 0.036 m³ environmental chamber used in this study; (vi) minimal source of errors: because no mechanical loading device is needed for this system, errors associated with a mechanical loading do not exist; (vii) specimen-blind test: because the field thermal cracking phenomena are simulated reasonably well with the test parameters, test results are believed to be representative of the field thermal cracking behavior and believed to be independent of specimen type, e.g., modified or unmodified; and (viii) simple procedure: overall, there is minimal operator interference during the test, making the procedure simple and straight-forward.

While the above description contains many specificities, these should not be construed as limitations on the scope of the invention, but rather as exemplification of certain preferred embodiments. Numerous other variations of the present invention are possible, and is not intended herein to mention all of the possible equivalent forms or ramifications of this invention. Various changes may be made to the present invention without departing from the scope or spirit of the invention.

What is claimed:

1. A device for characterizing construction materials, comprising:
   (a) a metal ring;
   (b) at least one strain gauge attached to said metal ring;
   (c) a processor in communication with said at least one strain gauge for recording and processing data from said at least one strain gauge; and
   (d) an environmental chamber for controlling the temperature to which said device and said materials are exposed.

2. The device of claim 1, further comprising a mold for forming a test specimen.

3. The device of claim 2, wherein said mold further comprises:
   (a) a substantially flat base plate;
   (b) a centering plate mountable on said base plate; and
   (c) a first specimen support and a second specimen support mountable on said base plate and defining a gap between said centering plate and said specimen supports for accommodating said test specimen.

4. The device of claim 3, wherein said centering plate further comprises a plurality of apertures passing completely through said plate and wherein said mold further comprises at least two dowel pins mountable to said base plate for stabilizing said centering plate by passing said dowel pins through said plurality of apertures.

5. The device of claim 3, wherein said specimen supports are secured to said base plate by a plurality of shoulder bolts.

6. The device of claim 1, further comprising at least one thermocouple attached to said metal ring, and wherein said thermocouple is in communication with said processor.

7. The device of claim 1, further comprising at least one module for amplifying the signal of said strain gauge, and wherein said module is in communication with said processor.

8. The device of claim 1, wherein said metal ring is an aluminum ring having an outer diameter of about 50.8 mm, a height of about 12.7 mm, and a thickness of about 1.65 mm.

9. The device of claim 1, wherein said construction material is asphalt binder.

10. A system for characterizing construction materials, comprising:
    (a) a metal ring;
    (b) at least one strain gauge attached to said metal ring;
    (c) at least one thermocouple attached to said metal ring;
    (d) at least one signal amplifying module in communication with said strain gauge and said thermocouple;
    (e) a processor in communication with said signal amplifying module for recording and processing data from said strain gauge and said thermocouple;
    (f) a mold for forming a test specimen, and wherein said mold further comprises:
       (i) a substantially flat base plate;
       (ii) a centering plate mountable on said base plate; and
       (iii) a first specimen support and a second specimen support mountable on said base plate and defining a gap between said centering plate and said specimen supports for accommodating said test specimen; and
    (g) an environmental chamber for controlling the temperature to which said device and said materials are exposed.

11. A method for characterizing a material, comprising the steps of:
    (a) creating a ring-shaped specimen of said material;
    (b) placing said specimen around a metal ring having at least one strain gauge attached to said ring such that said specimen is in contact with said ring;
    (c) attaching said strain gauge to a processor for gathering and processing information from said strain gauge;
    (d) placing the specimen and said metal ring inside of an environmental chamber;
    (e) lowering the temperature of said environmental chamber until said specimen cracks; and
    (f) utilizing said processor to process said information from said strain gauge.

12. The method of claim 11, further comprising the step of attaching a thermocouple to said ring and to said processor.

13. The method of claim 11, further comprising the step of attaching said strain gauge to a module for amplifying the signal of said strain gauge prior to attaching said strain gauge to said processor.

14. The method of claim 12, further comprising the step of attaching said thermocouple to a module for amplifying the signal of said thermocouple prior to attaching said thermocouple to said processor.

15. The method of claim 11, wherein said construction material is asphalt binder.

* * * * *